(12) United States Patent
Skloss et al.

(10) Patent No.: US 9,874,622 B2
(45) Date of Patent: Jan. 23, 2018

(54) HYPERPOLARIZED MEDIA TRANSPORT VESSEL

(71) Applicants:General Electric Company, Schenectady, NY (US); The United States of America, As Represented By The Secretary, Department of Health and Human Services Office of Technology Transfer, National Institutes of Health, Washington, DC (US)

(72) Inventors: Timothy William Skloss, Waukesha, WI (US); Jonathan Alan Murray, Dousman, WI (US); Jan Henrik Ardenkjaer-Larsen, Frederiksberg C (DK); Murali K. Cherukuri, Potomac, MD (US); Marcelino Bernardo, Germantown, MD (US); Nallathamby Devasahayam, Germantown, MD (US)

(73) Assignee: General Electric Company, Schenectady, NY (US)

( * ) Notice: Subject to any disclaimer, the term of this patent is extended or adjusted under 35 U.S.C. 154(b) by 972 days.

(21) Appl. No.: 14/038,948

(22) Filed: Sep. 27, 2013

(65) Prior Publication Data

US 2015/0091573 A1    Apr. 2, 2015

(51) Int. Cl.
*G01R 33/28* (2006.01)
*G01R 33/56* (2006.01)
*A61B 5/055* (2006.01)

(52) U.S. Cl.
CPC .......... *G01R 33/5601* (2013.01); *A61B 5/055* (2013.01); *G01R 33/282* (2013.01); *A61B 2560/06* (2013.01)

(58) Field of Classification Search
CPC   A61B 2560/06; A61B 5/055; G01R 33/5601; G01R 33/282
See application file for complete search history.

(56) References Cited

U.S. PATENT DOCUMENTS 5,209,068 A * 5/1993 Saji .................. F25B 21/00
 505/891
5,612,103 A  3/1997 Driehuys et al.
(Continued)

FOREIGN PATENT DOCUMENTS

WO    0050914 A1   8/2000
WO  2004090563 A1  10/2004
(Continued)

OTHER PUBLICATIONS

European Search Report and Written Opinion issued in connection with corresponding EP Application No. 14185164.2-1506 dated Aug. 11, 2015.
(Continued)

*Primary Examiner* — Clayton E Laballe
*Assistant Examiner* — Ruifeng Pu

(57) ABSTRACT

A system and method for transporting a hyperpolarized substance is disclosed. A transport vessel for transporting such a hyperpolarized substance includes a vessel housing, a chamber formed within the vessel housing that is configured to receive a container holding a hyperpolarized substance, and an electromagnet configured to generate a magnetic containment field about the chamber when a current is supplied thereto, the magnetic containment field comprising a homogeneous magnetic field. The transport vessel also includes a non-magnetic power source to supply the current to the electromagnet and a control circuit configured to selectively interrupt the supply of current to the electromagnet so as to control generation of the magnetic containment
(Continued)

field, with the transport vessel being magnetically inert when the supply of current to the electromagnet is interrupted by the control circuit.

18 Claims, 6 Drawing Sheets

(56) References Cited

U.S. PATENT DOCUMENTS

| | | | |
|---|---|---|---|
| 6,008,644 | A | 12/1999 | Leunbach et al. |
| 6,108,574 | A | 8/2000 | Ardenkjaer-Larsen |
| 6,128,918 | A | 10/2000 | Deaton et al. |
| 6,269,648 | B1 | 8/2001 | Hasson et al. |
| 6,278,893 | B1 | 8/2001 | Ardenkjaer-Larson et al. |
| 6,311,086 | B1 | 10/2001 | Ardenkjaer-Larsen et al. |
| 6,356,080 | B1 | 3/2002 | Daniels |
| 6,423,387 | B1 | 7/2002 | Zollinger et al. |
| 6,566,875 | B1 | 5/2003 | Hasson et al. |
| 6,667,008 | B2 | 12/2003 | Zollinger et al. |
| 8,020,694 | B2 | 9/2011 | Hasson et al. |
| 2003/0033830 | A1* | 2/2003 | Kuzma ............... F25J 1/0276 62/601 |
| 2003/0124732 | A1 | 7/2003 | Axelsson et al. |
| 2003/0157020 | A1 | 8/2003 | Petersson et al. |
| 2003/0212323 | A1 | 11/2003 | Petersson et al. |
| 2004/0066193 | A1 | 4/2004 | Ardenkjaer-Larsen et al. |
| 2004/0171928 | A1 | 9/2004 | Petersson et al. |
| 2006/0173283 | A1 | 8/2006 | Axelsson et al. |
| 2009/0016964 | A1* | 1/2009 | Kalechofsky ...... A61K 49/1815 424/9.3 |

FOREIGN PATENT DOCUMENTS

| | | |
|---|---|---|
| WO | 2006011809 A1 | 2/2006 |
| WO | 2006011810 A2 | 2/2006 |
| WO | 2006011811 A2 | 2/2006 |
| WO | 2006054903 A2 | 5/2006 |

OTHER PUBLICATIONS

EP Search Report dated Mar. 3, 2015 in relation to corresponding EP application 14185164.2.
Hiebel et al., "Magnetized boxes for housing polarized spins in homogeneous fields," Journal of Magnetic Resonance 204, 2010, pp. 37-49.

* cited by examiner

HYPERPOLARIZED MEDIA TRANSPORT VESSEL

BACKGROUND OF THE INVENTION

Embodiments of the invention relate generally to a hyperpolarized media for use in magnetic resonance imaging (MRI) and nuclear magnetic resonance (NMR) spectroscopy and, more particularly, to a vessel for transporting such a hyperpolarized media from a production source to an imaging system.

MRI and NMR spectroscopy are techniques that exploit the magnetic properties of certain atomic nuclei. With particular regard to MRI, a substance such as human tissue is subjected to a uniform magnetic field (polarizing field $B_0$), causing the individual magnetic moments of the spins in the tissue to attempt to align with this polarizing field, but precess about it in random order at their characteristic Larmor frequency. If the substance, or tissue, is subjected to a magnetic field (excitation field $B_1$) which is in the x-y plane and which frequency is near the Larmor frequency, the net aligned moment, or "longitudinal magnetization", $M_z$, may be rotated, or "tipped", into the x-y plane to produce a net transverse magnetic moment $M_t$. A signal is generated by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques. It is desirable that the imaging process, from data acquisition to reconstruction, be performed as quickly as possible for improved patient comfort and throughput.

One drawback to MRI and NMR spectroscopy is that they lack sensitivity due to the normally very low polarization of the nuclear spins of the samples used and/or substances being imaged. A number of techniques exist to improve the polarization of nuclear spins in the solid phase. These techniques are known as hyperpolarization techniques and lead to an increase in sensitivity. In hyperpolarization techniques, a sample of an imaging agent, for example $^{13}C$ Pyruvate or another similar polarized metabolic imaging agent, is introduced or injected into the subject being imaged. As used herein, the term "polarize" refers to the modification of the magnetic properties of a material for further use in MRI. Further, as used herein, the term "hyperpolarized" refers to polarization to a level over that found at room temperature and 1 T.

However, while hyperpolarized media is highly effective in improving the polarization of nuclear spins for MRI and NMR spectroscopy, it is recognized that the magnetic polarization of the hyperpolarized media has a short lifetime—with relaxation occurring in a matter of seconds to minutes, therefore requiring the media to be used in the MRI as soon as possible after hyperpolarization. This short lifetime of the magnetic polarization of the hyperpolarized media can be problematic since the polarized sample is often transported to the MRI unit from a hyperpolarizing apparatus that is located outside of the MRI imaging suite, requiring an operator to physically transport the hyperpolarized media from the hyperpolarizer to the MRI unit.

The short lifetime of the hyperpolarized media can be further negatively affected if the hyperpolarized media is not maintained in a suitable magnetic field. That is, movement of the media through a zero magnetic field or low background magnetic field below 1-2 Gauss (e.g., the background magnetic field generated by the MRI unit) can further shorten the lifetime of the hyperpolarized media. In order to address this problem, one solution has been to provide a specially designed vessel for transporting the hyperpolarized media between the hyperpolarizing apparatus and the MRI unit.

In one prior art vessel, a hollow transport vessel was designed with permanent magnetic material arranged inside designed to generate a suitable and stable background magnetic field for transporting the hyperpolarized media from the hyperpolarizer apparatus to the MRI unit, so as to maintain the hyperpolarized state of the media. However, such a permanent magnet transport vessel has several drawbacks, including: an inability to control the strength of the magnetic field generated by the vessel, significant inhomogeneity of the background magnetic field created inside the vessel, and the inability to turn the magnetic field off—which can cause the device to be interact with the MRI magnet with great force when brought in the vicinity of the MRI unit, such as by being attracted to or expelled from the magnet or being caused to twist/torque in the presence of the magnet.

Therefore, it is desirable to provide a transport solution that can safely and efficiently provide a suitable background magnetic field that is stable (homogenous magnetic field around hyperpolarized media) and preserves the lifetime of the hyperpolarized media. It would further be desirable for such a transport solution to be made of non-magnetic materials and equipped with a mechanism that enables selective generation of such a background magnetic field, so as to provide for disengaging of the magnetic field when necessary.

BRIEF DESCRIPTION OF THE INVENTION

In accordance with one aspect of the invention, a transport vessel for transporting a hyperpolarized substance includes a vessel housing, a chamber formed within the vessel housing that is configured to receive a container holding a hyperpolarized substance, and an electromagnet configured to generate a magnetic containment field about the chamber when a current is supplied thereto, the magnetic containment field comprising a homogeneous magnetic field. The transport vessel also includes a non-magnetic power source to supply the current to the electromagnet and a control circuit configured to selectively interrupt the supply of current to the electromagnet so as to control generation of the magnetic containment field, with the transport vessel being magnetically inert when the supply of current to the electromagnet is interrupted by the control circuit.

In accordance with another aspect of the invention, a device for transporting a hyperpolarized substance includes a vessel housing, a chamber formed within the vessel housing that is configured to receive a container holding a hyperpolarized substance, and an electromagnet configured to generate a magnetic containment field about the chamber when a current is supplied thereto, the magnetic containment field comprising a homogeneous field about the container. The device also includes a non-magnetic power source to supply the current to the electromagnet and a safety circuit configured to selectively interrupt the supply of current to the electromagnet in an automated fashion so as to control generation of the magnetic containment field, with the safety circuit further including a pressure activated safety switch configured to interrupt the supply of current to the electromagnet when a pressure applied to the safety switch is less than a threshold pressure value.

In accordance with yet another aspect of the invention, a method for transporting hyperpolarized substance includes securing a container holding a hyperpolarized substance within chamber formed in a transport vessel and generating a magnetic containment field about the chamber and about the container by way of an electromagnet of the transport vessel, the electromagnet configured to generate a homogeneous magnetic containment field having a controlled polarity that is free of switching between positive and negative charges so as to prolong a hyperpolarized state of the hyperpolarized substance. The method also includes selectively terminating the magnetic containment field in an automated fashion based upon a sensing of one or more parameters exceeding or falling below a pre-determined threshold value, the magnetic containment field being selectively terminated by way of a safety circuit of the transport vessel.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Embodiments of the invention provide a transport device or vessel that is configured to preserve hyperpolarization of a media when transporting the media in a hyperpolarized state, such as between a hyperpolarizer device and a magnetic resonance imaging (MRI) system, and provide for safe use of the vessel in the vicinity of the MRI system. While the transport vessel is described below as being used to transport a hyperpolarized media to an MRI system for use in an image acquisition performed thereby, it is recognized that the hyperpolarized media could be used in conjunction with other imaging techniques in which use of a hyperpolarized media is desired, such as nuclear magnetic resonance (NMR) spectroscopy for example.

Figure 1:
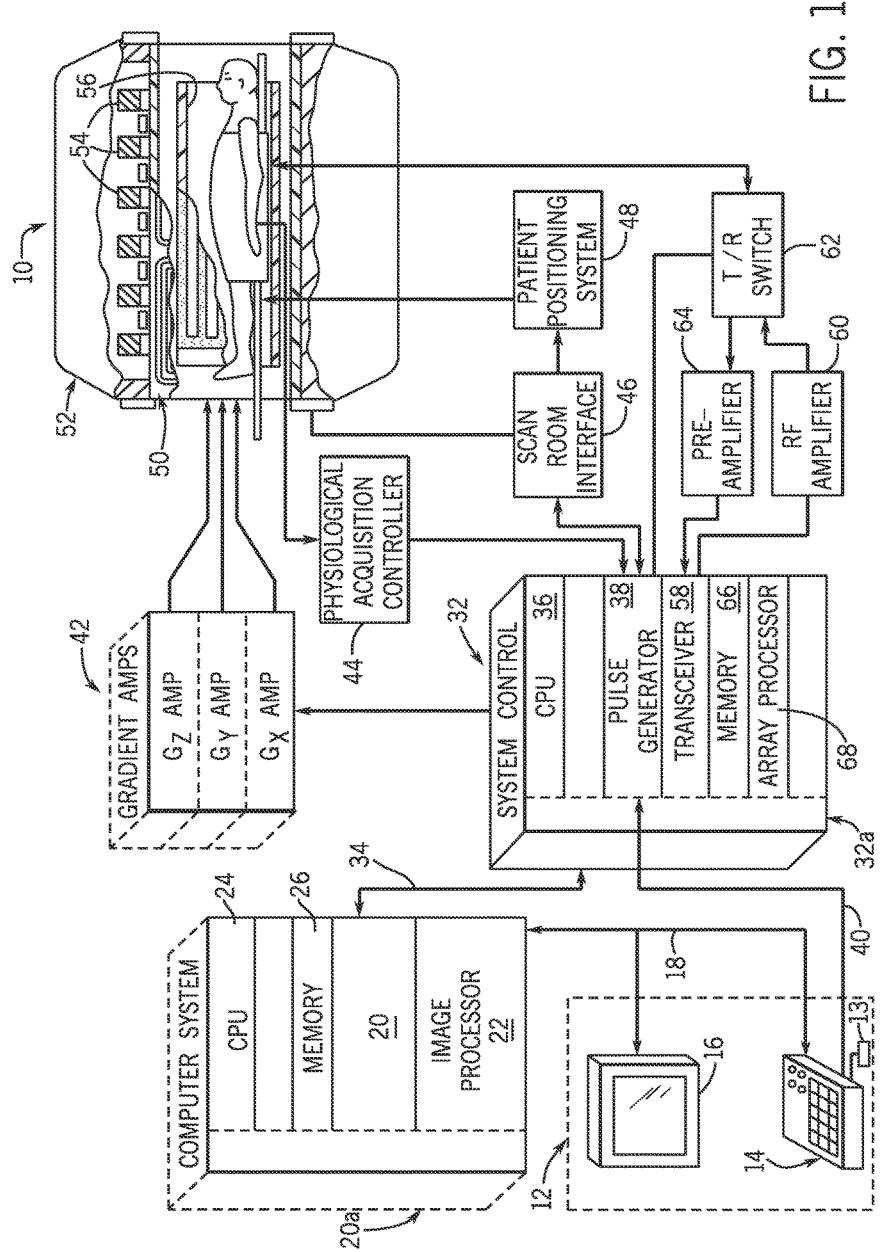
FIG. 1 is a schematic block diagram of an exemplary MR imaging system for use with an embodiment of the invention.

Referring to FIG. 1, the major components of a magnetic resonance imaging (MRI) system 10 incorporating an embodiment of the invention are shown. The operation of the system is controlled for certain functions from an operator console 12 which in this example includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These modules include an image processor module 22, a CPU module 24 and a memory module 26, known in the art as a frame buffer for storing image data arrays. The computer system 20 communicates with a separate system control 32 through a high speed serial link 34. The input device 13 can include a mouse, joystick, keyboard, track ball, touch activated screen, light wand, voice control, card reader, push-button, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a resonance assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12 or as otherwise directed by the system software, this image data may be archived in long term storage or it may be further processed by the image processor 22 and conveyed to the operator console 12 and presented on the display 16.

In using the MRI system 10 in acquiring MR image data, a hyperpolarized media or substance may be employed to improve the polarization of nuclear spins in the solid phase, so as to increase the sensitivity of signal acquisition and provide better contrast in images that are reconstructed, with additional functionality being provided in/on the MRI system 10 to enable signal acquisition from hydrogen nuclei and/or nuclei other than hydrogen (as might be encountered in spectroscopy employing a hyperpolarized media or substance). The hyperpolarized substance, such as $^{13}$C Pyruvate or another similar polarized metabolic imaging agent is introduced or injected into the subject being imaged. It is recognized that the magnetic polarization of the hyperpolarized media has a short lifetime—with relaxation occurring in a matter of seconds to minutes, therefore requiring the media to be used for MR image acquisition as soon as possible after hyperpolarization. As such, it is desirable to provide a vessel for transporting the hyperpolarized substance from a hyperpolarizing apparatus at which the substance is polarized to the MRI system for providing to the subject. The transport vessel maintains the hyperpolarized media in a suitable magnetic field so as to prolong the magnetic polarization of the hyperpolarized substance. It is also desirable for such a transport vessel to made of non-magnetic materials and equipped with a mechanism that enables selective generation of such a background magnetic field, so as to prevent interaction between the vessel and the MRI magnet that could result in a twisting/torquing of the vessel in the presence of the magnet—thereby providing for safe use of the vessel.

Figure 2:
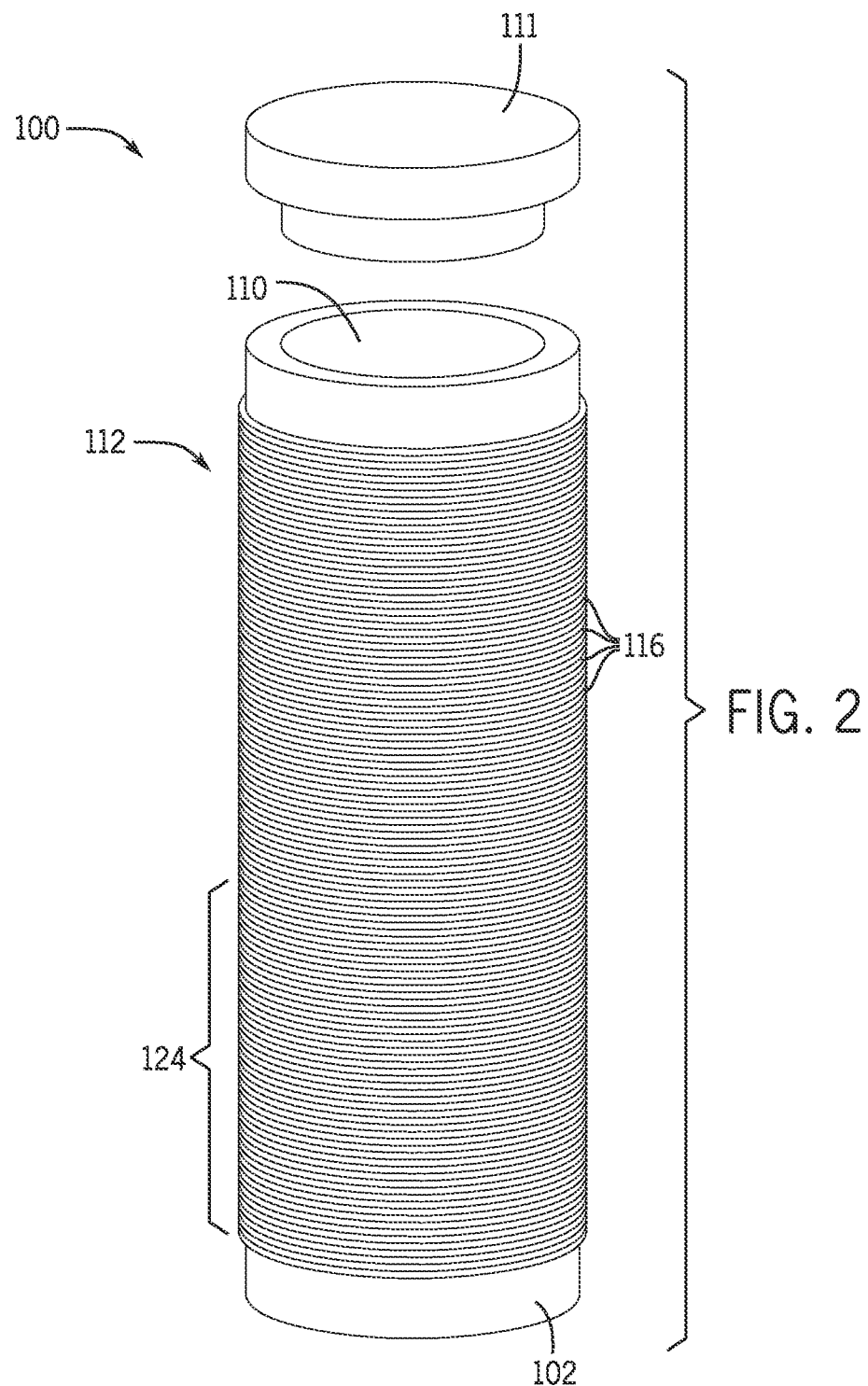
FIGS. 2 and 3 are views of a transport vessel for transporting a hyperpolarized substance, such as for use in an MR image acquisition performed using the MR imaging system of FIG. 1, according to an embodiment of the invention.
Figure 3:
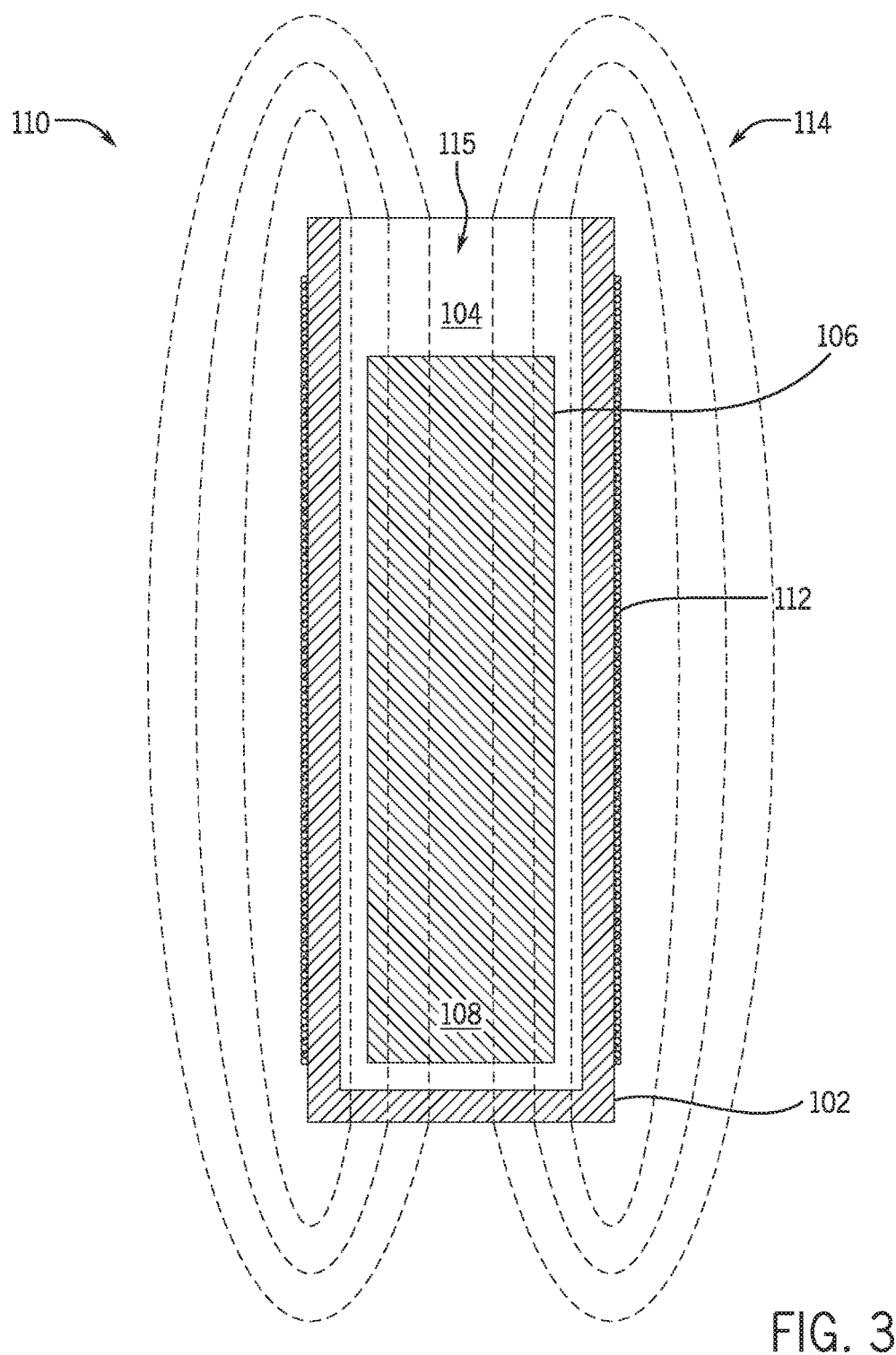

Referring to FIGS. 2 and 3, a hyperpolarized media transport vessel 100 is shown according to an exemplary embodiment of the invention. The vessel 100 includes a non-magnetic vessel housing 102 that is constructed to form and surround a hollow interior or chamber 104. The chamber 104 is sized and shaped to receive a container 106 therein that holds a hyperpolarized media 108, such as an infusion syringe or flask for example, with the chamber 104 receiving the container 106 therein and providing suitable protection to the container for transport—such as by keeping the container 106 stationary within chamber 104. According to one embodiment, a non-magnetic filler material (not shown) can be employed to define the chamber 104 within housing 102, to snugly receive the container 106 therein and provide for safe/secure transport thereof.

The vessel housing 102 is compact and light enough to allow the operator to transport vessel 100 by hand, and may be any of a number of shapes or constructions, such as cylindrical, rectangular, or another functionally equivalent configuration. The vessel housing is composed of a suitable non-magnetic and medically acceptable material, such as Polyethylene (PE) for example, that provides protection to the container 106 while being inert to magnetic fields that may be present about the vessel 100—e.g., those generated by an MRI magnet—such that the vessel 100 does not interact with the magnetic field generated thereby (i.e., being attracted to/expelled from a magnetic field and/or being twisted torque by the magnetic field).

As shown in FIG. 2, the vessel housing 102 includes an opening 110 formed therein to provide for insertion of the container 106 into the vessel 100. According to one embodiment of the invention, a cover 111 is optionally provided that is positionable in the opening 110 to enclose the container within chamber 104 when it is desired to transport the container with vessel 100. While not shown in FIGS. 2 and 3, it is contemplated that vessel 100 may also include an outer covering (not shown) formed about the housing 102 in order to protect vessel 100 and to facilitate convenient and ergonomic transport.

Figure 4:
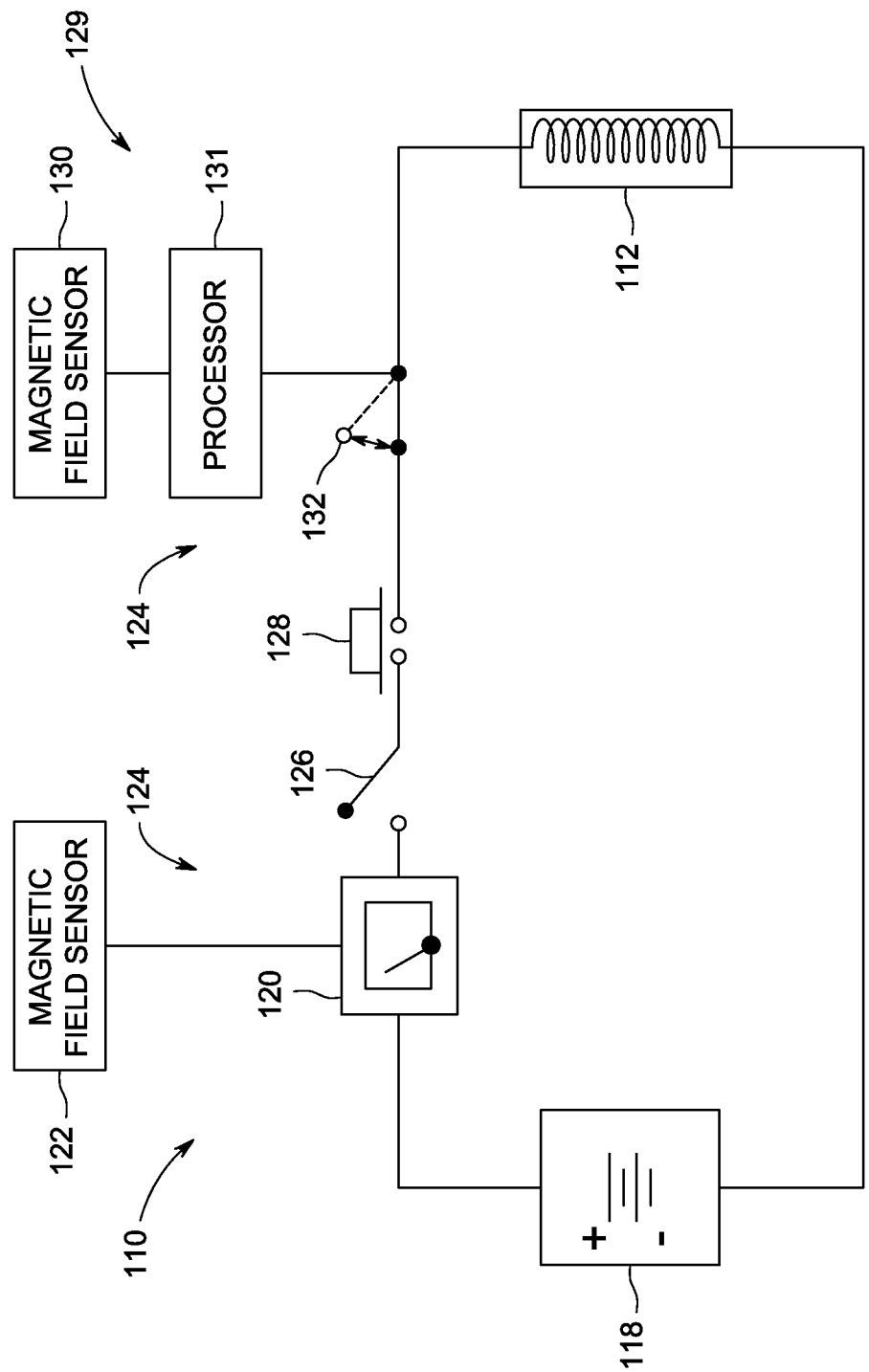
FIG. 4 is a schematic block diagram of an exemplary control circuit for use in the transport vessel of FIGS. 2 and 3, according to an embodiment of the invention.

As shown in FIG. 2, and in the block schematic diagram of FIG. 4, an electromagnet 112 is included in vessel 100 and formed on the housing 102 such that the electromagnet generally surrounds the chamber 104—with the electromagnet 112 being configured to generate a suitable and stable background magnetic field for transporting the hyperpolarized media within vessel 100, i.e., a magnetic containment field 114 that surrounds the chamber 104, so as to maintain the hyperpolarized state of the media. The electromagnet 112 can be any device which creates a magnetic field from electrical input. In the embodiment in FIG. 2, electromagnet 112 is in the form of a single solenoid coil formed from a plurality of windings of copper wire 116 that are wrapped around vessel housing 102 so as to encircle the chamber 104, with the solenoid 112 being housed within an electrically insulating outer cover (not shown) of the vessel 100 so as to be protected from the ambient environment. In operation, as shown in FIG. 3, the electromagnet 112 generates a magnetic containment field 114 about chamber 104, with the magnetic containment field 114 including a homogenous magnetic field section 115 that surrounds hyperpolarized media 108 in container 106—as indicated by the parallel magnetic field lines 114 within electromagnet 112. The homogenous magnetic field section 115 of magnetic containment field 114 has a controlled polarity that is free of switching between positive and negative charges.

Figure 5:
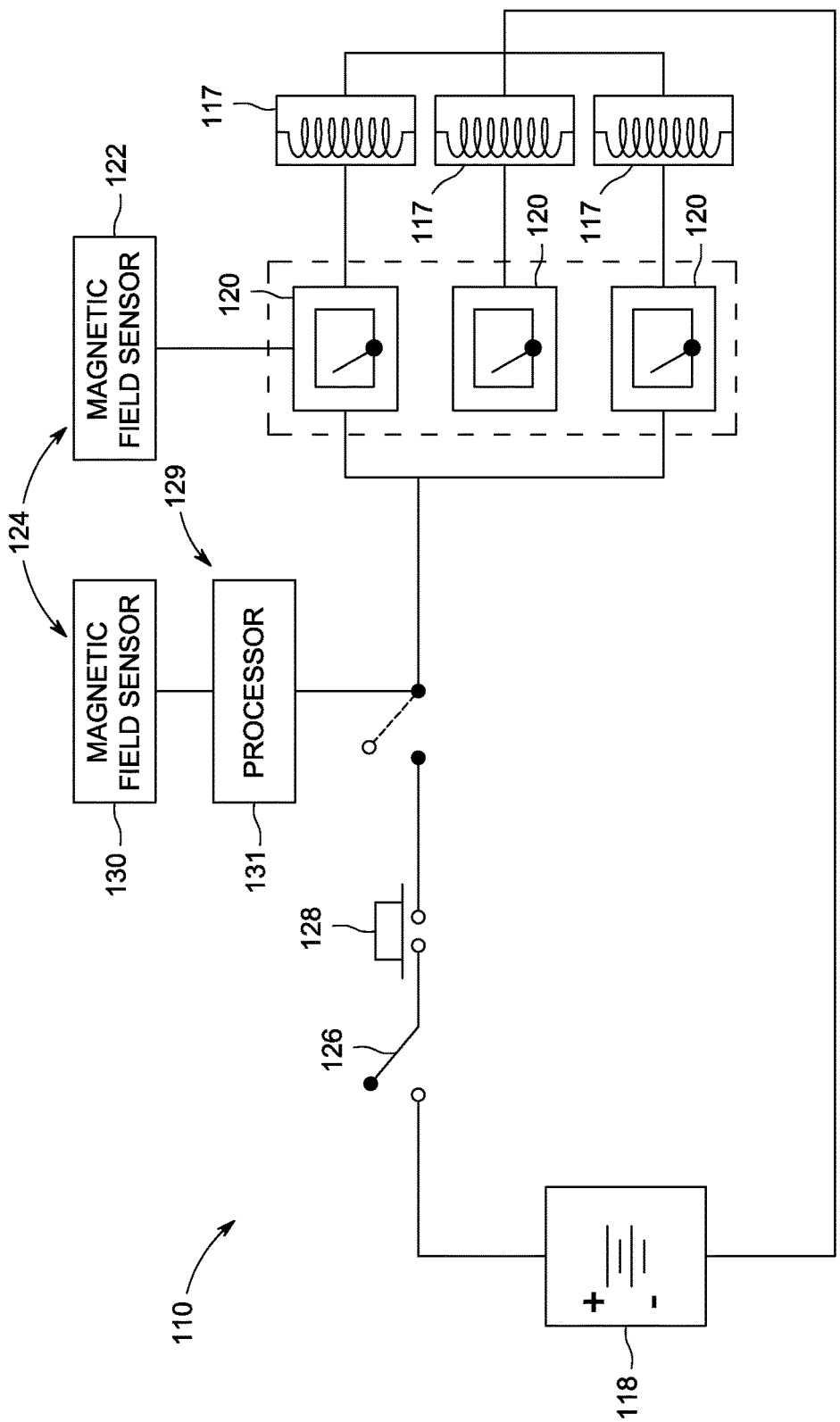
FIG. 5 is a schematic block diagram of an exemplary control circuit for use in the transport vessel of FIGS. 2 and 3, according to another embodiment of the invention.
Figure 6:
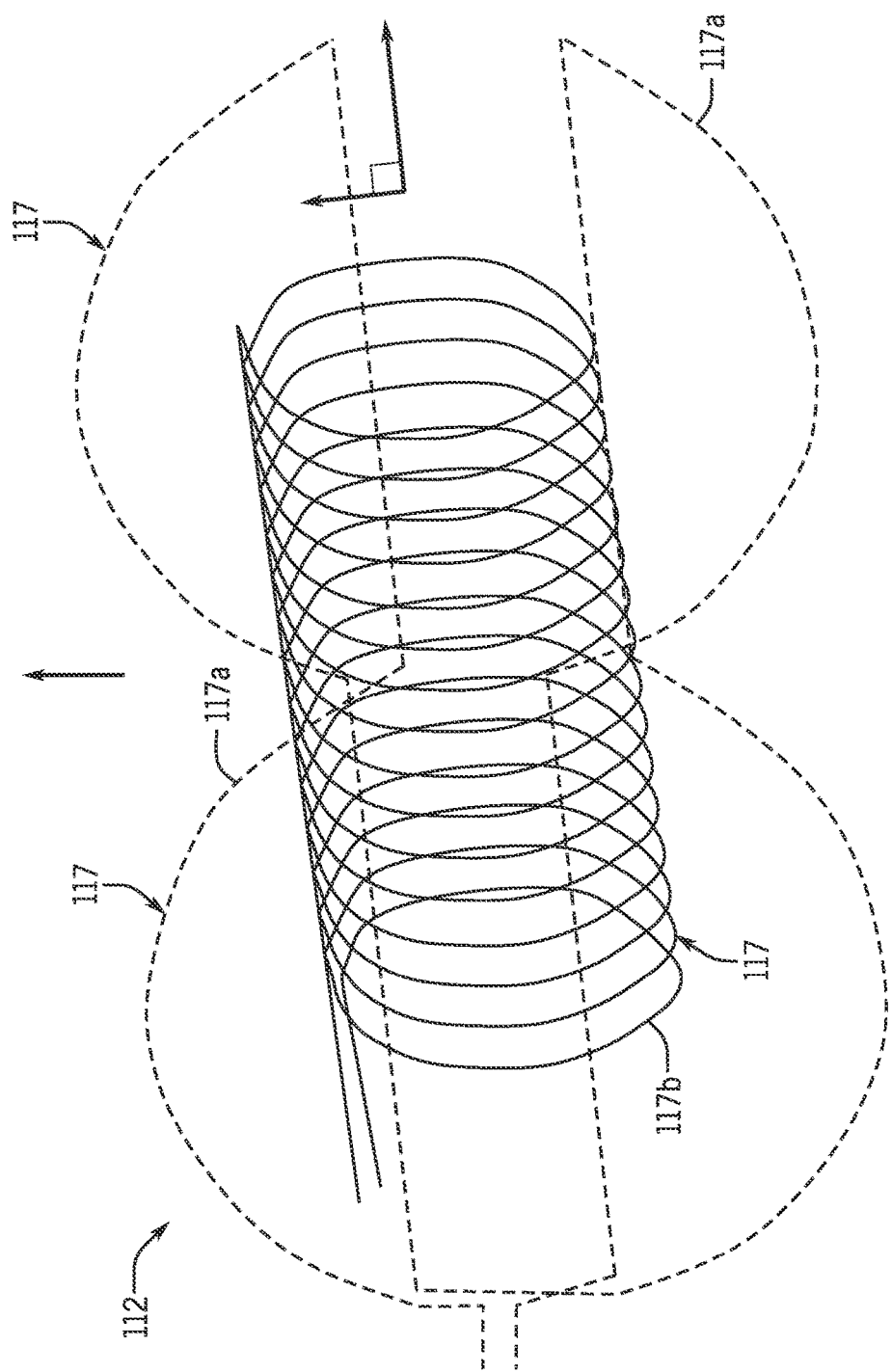
FIG. 6 is a view of an electromagnet of a transport vessel for use with the control circuit of FIG. 5, according to an embodiment of the invention.

While electromagnet 112 is described above as being in the form of a single solenoid coil, it is recognized that other coil configurations could be employed. That is, according to one embodiment of the invention, electromagnet 112 can be formed of multiple coils/coil portions 117—such as shown in an embodiment of the vessel illustrated in FIGS. 5 and 6—that are each individually controllable (e.g., with each with individual current control circuits), so as to provide for effecting magnetic transport fields of varying qualities in multiple dimensions. According to an exemplary embodiment, the coils/coil portions 117 are arranged so as to provide a 3-axis electromagnet, such as by winding two saddle-shaped coils 117a on cylinder(s) concentric to the solenoid coil 117b and with their field axes oriented perpendicular to each other, as illustrated in FIG. 6.

As shown in FIG. 4, vessel 100 also includes a power source 118 and a power control 120 to selectively provide power to the electromagnet 112. In one embodiment, power supply 118 is a non-magnetic battery, such as a lithium-ion polymer (LiPo) single cell battery, but it is recognized that the power supply 118 may be any non-magnetic power source that does not interact with a surrounding magnetic field, such as one generated by an MRI magnet. It is also contemplated power supply 118 is large enough to provide sufficient power to electromagnet 112 for at least one use, and preferably multiple uses, for transporting a hyperpolarized media from its production source to its location for use in an MR image acquisition. The power control 120 controls the amount of current flowing from power source 118 to electromagnet 112, thereby allowing an adjustment of a strength of the magnetic containment field 114 generated by the electromagnet 112, such as between a value of 0 and 100 Gauss. The power control 120 advantageously provides for dynamic adjustment of the magnetic containment field 114, such that the hyperpolarization of the hyperpolarized media being transported can be better preserved, with adjustment of a strength of the field 114 accounting for variation in system components (such as power source 118), or to compensate for background magnetic field variation in the environment. It is contemplated power control 120 could be as simple as a basic rheostat, or as intricate as a separate control system controlled by a remote operator. Additionally, in an embodiment where electromagnet 112 is formed from multiple, individually addressable coils/coil portions 117, such as shown in FIG. 5, power control 120 may include a number of individual current control circuits so as to enable the supplying of a desired current to each of the coils 117 to effect magnetic transport fields of varying qualities in multiple dimensions. In addition, individual current control circuits may be configured to individually address separate and distinct coils to provide active shielding around the electromagnet 112. That is, separate coils/coil portions 117 may be configured to provide additional cancellation of the effects of ambient magnetic fields on electromagnet 112, further protecting homogenous region 115 and the hyperpolarized media 108 contained therein and reducing the interaction between the electromagnet 112 and the ambient magnetic fields generated by MR magnet 54.

According to one embodiment, and in order to make an efficient transport device 100, it is contemplated that the strength and homogeneity of the magnetic containment field 114 may be calibrated by positioning a magnetic field sensor 122 (hall effect), or a separate magnetic field sensor, inside chamber 104 and manipulating power control 120 to achieve the desired field strength. The transport field can be "locked" at a specific field strength based on active feedback provided by the magnetic field sensor 122 to the power/current control circuit 120. This approach could be used to "shield" the hyperpolarized media from external fluctuating fields on the order of kilohertz and lower with an appropriately designed feedback circuit.

As further shown in FIG. 4, a control circuit 124 (i.e., "safety circuit") is included in the vessel 100 that provides for selective operation thereof—with the control circuit 124 enabling selective interruption of the supply of current to the electromagnet 112 so as to control generation of the magnetic containment field. That is, it is recognized that disengaging/termination of the magnetic containment field is necessary for vessel 100 in order for the vessel to be brought into the vicinity of an MRI system (i.e., the magnet of the MRI system)—as continued generation of the magnetic containment field in the presence of an MRI system could cause the device to be twisted/torque responsive to the field generated by the MRI magnet when brought in the vicinity of the MRI system (i.e., as the electromagnet attempts to align its magnetic axis with the MRI magnet's field) thereby causing a person to lose hold of the vessel. According to the embodiment illustrated in FIG. 4, control circuit 124 includes a plurality of switches and sensor(s) that function to selectively interrupt the supply of current to the electromagnet 112. Included in control circuit 124 is a manually activated power switch 126. The manually activated power switch 126 is movable by an operator to provide for turning the electromagnet on and off as desired.

Control circuit 124 also includes a number of switches/sensors therein that provide for an "automatic" interruption of current to the electromagnet 112 under certain predetermined conditions. Such automated features are highly desirable as additional safeguards, as they provide for disengaging/termination of the magnetic containment field 114 in situations where the operator forgets to terminate a supply of power to the electromagnet 112 (e.g., forgets to manually shut off power to electromagnet 112 by way of power switch 126) or where some unforeseen event prevents the operator from terminating a supply of power to the electromagnet 112.

As one safeguard for providing automatic interruption of current to the electromagnet 112, control circuit 124 includes a pressure safety switch 128 that functions to selectively interrupt current flow. The pressure safety switch 128 is configured as a "deadman switch" that enables a flow of current from power source 118 to electromagnet 112—so as to create magnetic containment field 114—only when the operator is applying an amount of pressure to safety switch 128 that is greater than a minimum threshold pressure value. The threshold pressure value is the amount of force required to depress the safety switch 128 button, which creates a short across safety switch 128 in control circuit 124, thus allowing current flow from power source 118 to electromagnet 112, and creating electromagnetic containment field 114. In the situation where the operator releases vessel 100 or an MRI magnet causes the vessel 100 to leave the operator's grasp (i.e., the MRI magnet attracts the vessel 100 and causes it to be pulled from the grasp of the operator), the pressure applied to safety switch 128 will be less than the threshold pressure value, causing a disconnect in control circuit 124, thereby interrupting current flow between power source 118 and electromagnet 112 and consequently interrupting magnetic containment field 114, ensuring magnetic containment field 114 will not further interact with any surrounding magnetic fields.

As another safeguard for providing automatic interruption of current to the electromagnet 112, control circuit 124 includes a magnetic field sensor/current interruption circuit 129 that is composed of a magnetic field sensor 130 (with it being recognized that the sensor 130 may be separate from sensor 122, as shown in FIG. 4, or the same sensor), a processor 131, and a magnetic field safety switch 132. The magnetic field sensor 130 detects the strength of an ambient magnetic field in an immediate area around vessel 100, while processor 131 is operably coupled to magnetic field sensor 130 to receive an input regarding the ambient field strength. The processor 131 is programmed to cause magnetic field safety switch 132 to open when the ambient magnetic field strength is greater than a threshold value—with the threshold value being set in processor 131 by the operator. The threshold value is contemplated to be a maximum magnetic field strength that does not cause a potentially dangerous interaction between background magnetic fields and vessel 100. In operation of vessel 100, current is supplied to electromagnet 112 by power source 118 until magnetic field sensor 130 detects a background magnetic field greater than a threshold value, after which processor 131 causes magnetic field safety switch 132 to open, selectively interrupting current flow to electromagnet 112, thereby interrupting magnetic containment field 114. The circuit 129 thus ensures that magnetic containment field 114 does not interact with background magnetic fields above the threshold value, such as those background fields inherent around an MRI magnet, thereby preventing the transport vessel 100 from being expelled from or pulled toward the MRI magnet.

Therefore, according to one embodiment of the invention, a transport vessel for transporting a hyperpolarized substance includes a vessel housing, a chamber formed within the vessel housing that is configured to receive a container holding a hyperpolarized substance, and an electromagnet configured to generate a magnetic containment field about the chamber when a current is supplied thereto, the magnetic containment field comprising a homogeneous magnetic field. The transport vessel also includes a non-magnetic power source to supply the current to the electromagnet and a control circuit configured to selectively interrupt the supply of current to the electromagnet so as to control generation of the magnetic containment field, with the transport vessel being magnetically inert when the supply of current to the electromagnet is interrupted by the control circuit.

According to another embodiment of the invention, a device for transporting a hyperpolarized substance includes a vessel housing, a chamber formed within the vessel housing that is configured to receive a container holding a hyperpolarized substance, and an electromagnet configured to generate a magnetic containment field about the chamber when a current is supplied thereto, the magnetic containment field comprising a homogeneous field about the container. The device also includes a non-magnetic power source to supply the current to the electromagnet and a safety circuit configured to selectively interrupt the supply of current to the electromagnet in an automated fashion so as to control generation of the magnetic containment field, with the safety circuit further including a pressure activated safety switch configured to interrupt the supply of current to the electromagnet when a pressure applied to the safety switch is less than a threshold pressure value.

According to yet another embodiment of the invention, a method for transporting hyperpolarized substance includes securing a container holding a hyperpolarized substance within chamber formed in a transport vessel and generating a magnetic containment field about the chamber and about the container by way of an electromagnet of the transport vessel, the electromagnet configured to generate a homogeneous magnetic containment field having a controlled polarity that is free of switching between positive and negative charges so as to prolong a hyperpolarized state of the hyperpolarized substance. The method also includes selectively terminating the magnetic containment field in an automated fashion based upon a sensing of one or more parameters exceeding or falling below a pre-determined threshold value, the magnetic containment field being selectively terminated by way of a safety circuit of the transport vessel.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A transport vessel for transporting a hyperpolarized substance, the transport vessel comprising:
   a vessel housing;
   a chamber formed within the vessel housing that is configured to receive a container holding a hyperpolarized substance;
   an electromagnet configured to generate a magnetic containment field about the chamber when a current is supplied thereto, the magnetic containment field comprising a homogeneous magnetic field;
   a non-magnetic battery to supply the current to the electromagnet; and
   a control circuit configured to selectively interrupt the supply of current to the electromagnet so as to control generation of the magnetic containment field;
   wherein the transport vessel is magnetically inert when the supply of current to the electromagnet is interrupted by the control circuit; and
   wherein the control circuit comprises:
   a magnetic field sensor configured to detect a strength of an ambient magnetic field in an area in which the transport vessel is located;
   a processor operably coupled to the magnetic field sensor so as to receive an input therefrom regarding the strength of the ambient magnetic field; and
   a magnetic field safety switch configured to interrupt the supply of current to the electromagnet; and
   wherein the processor is programmed to cause the magnetic field safety switch to open when the strength of the ambient magnetic field is greater than a threshold value, so as to interrupt the supply of current to the electromagnet.

2. The transport vessel of claim 1, wherein the control circuit comprises a pressure activated switch configured to interrupt the supply of current to the electromagnet when a pressure applied to the pressure activated switch is less than a threshold pressure value.

3. The transport vessel of claim 1, wherein the control circuit comprises a manually activated power switch movable by an operation to selectively interrupt the supply of current to the electromagnet.

4. The transport vessel of claim 1, further comprising a power control to control the supply of current from the non-magnetic battery to the electromagnet, such that a strength of the magnetic containment field may also be controlled.

5. The transport vessel of claim 4, wherein the electromagnet comprises a solenoid that receives current whose magnitude is controlled by the power control, so as to control a strength of the magnetic containment field.

6. The transport vessel of claim 5, wherein the solenoid comprises a number of coil portions and wherein the power control comprises a number of individual current control circuits, such that a supply of current to each of the coil portions is individually controllable, so as to enable the generation of magnetic containment fields of varying qualities in multiple dimensions.

7. The transport vessel of claim 6, wherein the number of coil portions are arranged so as to provide a 3-axis electromagnet having field axes oriented perpendicular to each other.

8. The transport vessel of claim 4, wherein a strength of the magnetic containment field is adjustable between 0 and 100 Gauss.

9. The transport vessel of claim 1, wherein the homogeneous magnetic containment field has a controlled polarity that is free of switching between positive and negative charges containment field is homogeneous within internal volume of receptacle surrounding hyperpolarized media.

10. A device for transporting a hyperpolarized substance, the transport device comprising:
- a vessel housing;
- a chamber formed within the vessel housing that is configured to receive a container holding a hyperpolarized substance;
- an electromagnet configured to generate a magnetic containment field about the chamber when a current is supplied thereto, the magnetic containment field comprising a homogeneous field about the container;
- a non-magnetic battery to supply the current to the electromagnet; and
- a safety circuit configured to selectively interrupt the supply of current to the electromagnet in an automated fashion so as to control generation of the magnetic containment field;
- wherein the safety circuit comprises:
- a magnetic field sensor configured to detect a strength of an ambient magnetic field in an area in which the transport vessel is located;
- a processor operably coupled to the magnetic field sensor so as to receive an input therefrom regarding the strength of the ambient magnetic field; and
- a magnetic field safety switch configured to interrupt the supply of current to the electromagnet;
- wherein the processor is programmed to cause the magnetic field safety switch to open when the strength of the ambient magnetic field is greater than a threshold value, so as to interrupt the supply of current to the electromagnet.

11. The transport device of claim 10, further comprising a power control to control the supply of current from the non-magnetic battery to the electromagnet, such that a strength of the magnetic containment field may also be controlled.

12. The transport device of claim 11, wherein the electromagnet comprises a solenoid having a number of coil portions; and wherein the power control comprises a number of individual current control circuits that individually control a supply of current to each of the number of coil portions, so as to enable the generation of magnetic containment fields of varying qualities in multiple dimensions.

13. The transport vessel of claim 10, further comprising a manually activated power switch movable by an operation to selectively interrupt the supply of current to the electromagnet.

14. The transport vessel of claim 10, wherein the homogeneous magnetic containment field has a controlled polarity that is free of switching between positive and negative charges containment field is homogeneous within internal volume of receptacle surrounding hyperpolarized media.

15. The transport vessel of claim 10, wherein the electromagnet comprises a solenoid coil.

16. A method for transporting hyperpolarized substance comprising:
- securing a container holding a hyperpolarized substance within a transport vessel, the container being positioned in a chamber formed in the transport vessel;
- generating a magnetic containment field about the chamber and about the container by way of an electromagnet of the transport vessel, the electromagnet configured to generate a homogeneous magnetic containment field having a controlled polarity that is free of switching between positive and negative charges so as to prolong a hyperpolarized state of the hyperpolarized substance;
- selectively terminating the magnetic containment field in an automated fashion based upon a sensing of one or more parameters exceeding or falling below a predetermined threshold value, the magnetic containment field being selectively terminated by way of a safety circuit of the transport vessel; and
- providing current to the electromagnet by way of a non-magnetic battery included in the transport vessel;
- wherein selectively terminating the magnetic containment field comprises:
- detecting a strength of an ambient magnetic field in an area in which the transport vessel is located by way of a magnetic field sensor in the safety circuit; and
- if the strength of the ambient magnetic field is greater than a magnetic field threshold value, then interrupting a supply of current to the electromagnet by opening a magnetic field safety switch in the safety circuit, such that the magnetic containment field is terminated.

17. The method of claim 16, wherein selectively terminating the magnetic containment filed comprises:
- determining a pressure applied to a pressure activated safety switch in the safety circuit; and
- if the pressure applied to the pressure activated safety switch is less than a threshold pressure value, interrupting a supply of current to the electromagnet by opening a pressure activated safety switch in the safety circuit, such that the magnetic containment field is terminated.

18. The method of claim 16, further comprising controlling a strength of the magnetic containment field between 0 and 100 Gauss by controlling a flow of current to the electromagnet.

* * * * *